United States Patent [19]

Zimmerman et al.

[11] Patent Number: 5,003,107
[45] Date of Patent: Mar. 26, 1991

[54] CATALYTIC METHOD FOR THE REDUCTIVE AMINATION OF POLY(OXYTETRAMETHYLE) GLYCOLS

[75] Inventors: Robert L. Zimmerman; John M. Larkin, both of Austin, Tex.

[73] Assignee: Texaco Chemical Company, White Plains, N.Y.

[21] Appl. No.: 452,146

[22] Filed: Dec. 18, 1989

[51] Int. Cl.$^5$ .............................. C07C 213/04
[52] U.S. Cl. .................. 564/475; 564/479; 564/480; 564/506; 502/305
[58] Field of Search ............ 564/479, 480, 475, 506; 502/305

[56] References Cited

U.S. PATENT DOCUMENTS

| | | | |
|---|---|---|---|
| 3,152,998 | 10/1964 | Moss | 502/315 |
| 3,436,359 | 4/1969 | Hubin et al. | 528/68 |
| 3,824,198 | 7/1974 | Smith et al. | 528/374 |
| 3,824,219 | 7/1974 | Smith et al. | 528/408 |
| 3,824,220 | 7/1974 | Smith et al. | 528/408 |
| 3,847,992 | 11/1974 | Moss | 560/480 |
| 4,642,303 | 2/1987 | Renken et al. | 564/506 |
| 4,742,179 | 5/1988 | Sanderson et al. | 568/913 |
| 4,758,681 | 7/1988 | Marquis et al. | 556/57 |
| 4,766,245 | 8/1988 | Larkin et al. | 564/475 |
| 4,833,213 | 5/1989 | Leir et al. | 528/38 |
| 4,873,380 | 10/1989 | Sanderson et al. | 568/914 |

*Primary Examiner*—Glennon H. Hollrah
*Assistant Examiner*—Mark W. Russell
*Attorney, Agent, or Firm*—Jack H. Park; Kenneth R. Priem; Carl G. Ries

[57] ABSTRACT

Poly(oxytetramethylene) diamines useful in the preparation of polyamide and polyurea elastomers are prepared by the catalytic reductive amination of a poly(oxytetramethylene) glycol feedstock under reductive amination conditions in the presence of ammonia and hydrogen using a hydrogenation/dehydrogenation catalyst composed of, on an oxide-free basis, about 70 to 75 wt. % of nickel, about 20 to about 25 wt. % of copper, about 0.5 to 5 wt. % of chromium and about 1 to 5 wt. % of molybdenum.

7 Claims, No Drawings

1

CATALYTIC METHOD FOR THE REDUCTIVE AMINATION OF POLY(OXYTETRAMETHYLE) GLYCOLS

BACKGROUND OF THE INVENTION

1. Technical Field of the Invention

This invention relates to a method for the catalytic reductive amination of a poly(oxytetramethylene) glycol in order to provide the corresponding poly(oxytetramethylene) diamine in high yield and with good selectivity.

More particularly, this invention relates to an improvement in the method for the catalytic reductive amination of a poly(oxytetramethylene) glycol in the presence of hydrogen and ammonia under reductive amination conditions wherein the reaction is conducted in the presence of a catalyst composed of nickel, copper, chromium and molybdenum and containing, on an oxide-free basis, about 70 to about 75 wt. % of nickel, about 20 to about 25 wt. % of copper, about 0.5 to 5 wt. % of chromium and about 1 to 5 wt. % of molybdenum.

Still more particularly, this invention relates to a process wherein a poly(oxytetramethylene) glycol, excess ammonia and hydrogen are passed through a bed of a pelleted nickel, copper, chromium, molybdenum catalyst on a continuous basis in order to continuously provide a reaction product comprising the poly(oxytetramethylene) diamine corresponding to the poly(oxytetramethylene) glycol feedstock.

2. Prior Art

Methods for the preparation and use of poly(oxytetramethyl) qlycols are disclosed in Smith et al. U.S. Pat. Nos. 3,824,198, 3,824,219, and 3,824,220, patented July 16, 1974. Other patents disclosing methods for making and using poly(oxytetramethyl) glycols and poly(oxytetramethyl) diamines include Hubin et al. U.S. Pat. No. 3,436,359 patented Apr. 1, 1969 and Leir et al. U.S. Pat. No. 4,833,213, patented May 23, 1989.

The catalyst to be used in conducting the process of the present invention is suitably a catalyst of the type disclosed in Moss et al. U.S. Pat. No. 3,151,115 wherein reductive amination catalysts are disclosed containing nickel, cobalt and copper or mixtures thereof and chromium oxide, molybdenum oxide, manganese oxide, thorium oxide and mixtures thereof.

The preferred catalyst disclosed by Moss et al. is a nickel, copper, chromia catalyst containing, on an oxide-free basis, from about 70 to 75 wt. % of nickel, about 20 to about 25 wt. % of copper and about 1 to about 5 wt. % of chromium.

Renken et al. U.S. Pat. No. 4,618,717, issued Oct. 21, 1986 is directed to a method for reductively aminating ethylene glycol monoalkyl ethers in order to provide the corresponding primary amines using a catalyst composed of about 50 to 90 wt. % of nickel, about 10 to 50 wt. % of copper and about 0.5 to 5 wt. % of an oxide of chromium, iron, titanium, thorium, zirconium, manganese, magnesium or zinc. Larkin et al. U.S. Pat. No. 4,766,245, issued Aug. 23, 1988 discloses a method for reductively aminating polyoxyalkylene diols and triols in the presence of a Raney nickel/aluminum catalyst.

The purification of tertiary butyl alcohol by the catalytic decomposition of impurities such as tertiary butyl hydroperoxide is disclosed in a series of patents. The catalyst of Marquis et al. U.S. Pat. No. 4,758,681, issued July 19, 1988, contains about 30 to 60 wt. % of nickel, about 5 to 40 wt. % of copper, about 1 to 30 wt. % of iron and about 0.5 to 10 wt. % of chromium. Sanderson et al. disclose the use of a catalyst containing 20 to 80 wt. % of iron, 5 to 40 wt. % of copper, 0.1 to 10 wt. % of chromium and 0.01 to 5 wt. % of cobalt for this purpose. In Sanderson et al. U.S. Pat. No. 4,742,179, the catalyst that is used for this purpose contains 1 to 20 wt. % of iron and 1 to 6 wt. % of chromium, the balance being composed of a mixture of nickel and copper, while the catalyst of Sanderson et al. U.S. Pat. No. 4,873,380, issued Oct. 10, 1989 is composed of 1 to 20 wt. % of barium, 1 to 6 wt. % of chromium and the balance a mixture of nickel and copper.

SUMMARY OF THE INVENTION

This invention relates to a method for preparing poly(oxytetramethylene) diamines. Poly(oxytetramethylene) diamines are useful for the preparation of polyamide and polyurea elastomers. The poly(oxytetramethylene) diamines are conveniently prepared from the corresponding poly(oxytetramethylene) glycols, commonly referred to as polytetrahydrofuran glycols. However, when the poly(oxytetramethylene) diamines are prepared by catalytic reductive amination of the corresponding poly(oxytetramethylene) glycols, using hydrogenation/dehydrogenation catalysts, and in particular, nickel hydrogenation/dehydrogenation catalysts, problems are normally encountered in obtaining both a good yield and a good selectivity in converting the poly(oxytetramethylene) glycol to the desired poly(oxytetramethylene) diamine product.

These and other problems are overcome in accordance with the present invention by conducting the reductive amination reaction in the presence of a catalyst composed of nickel, copper, chromium and molybdenum and containing, on an oxide-free basis, from about 70 to 75 wt. % of nickel, about 20 to about 25 wt. % of copper, about 0.5 to about 5 wt. % of chromium and about 1 to about 5 wt. % of molybdenum.

DETAILED DESCRIPTION

The starting materials for the present invention are a nickel, copper, chromia, molybdenum catalyst which may suitably be a powdered catalyst if the reaction is to be conducted in an autoclave on a batch basis or a pelleted catalyst if the reaction is to be conducted on a continuous basis in a continuous reactor. Also used as starting materials are ammonia, hydrogen and a poly(oxytetramethylene) glycol such as a poly(oxytetramethylene) glycol having the following formula:

$$HO-CH_2-CH_2-CH_2-CH_2-[-O-CH_2-CH_2-CH_2-CH_2-]_n-O-CH_2-CH_2-CH_2-CH_2-OH \quad (I)$$

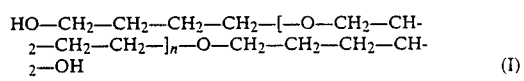

wherein n represents 0 or a positive number having a value of 1 to about 50.

In accordance with the present invention, a poly(oxytetramethylene) glycol feedstock is substantially quantitatively converted to the corresponding poly(oxytetramethylene) diamine with excellent yields and selectivities when the reaction is conducted in the presence of a catalyst composed of from about 70 to about 75 wt. % of nickel, about 20 to about 25 wt. % of copper, about 0.5 to about 5 wt. % of chromium and about 1 to about 5 wt. % of molybdenum.

More particularly, an especially preferred catalyst composition of the present invention is one containing from about 70 to about 78 wt. % of nickel, about 20 to about 25 wt. % of copper, about 0.5 to about 3 wt. % of chromium, and about 1 to about 3 wt. % of molybdenum.

The reductive amination reaction of the present invention is suitably conducted at a temperature within the range of about 150° to about 220° C. and a pressure of about 100 to about 10,000 psig., such as a pressure of about 100 to about 3,000 psig.

The reductive amination is conducted in the presence of ammonia. Suitably, from about 1 to about 300 moles of ammonia per mole of poly(oxytetramethylene) glycol are employed, and more preferably, from about 10 to about 150 moles of ammonia are employed per mole of poly(oxytetramethylene) glycol.

The reaction is also preferably conducted in the presence of added hydrogen. The amount of added hydrogen used may be about 0.1 to about 10 mole per mole of poly(oxytetramethylene) glycol. Preferably, from about 0.5 to about 80 mole of hydrogen per mole of poly(oxytetramethylene) glycol will be employed.

The process of the present invention may be conducted batch-wise using an autoclave containing powdered catalyst, in which case the residence time is suitably from about 0.5 to about 5 hours.

More preferably, the reaction is conducted on a continuous basis using a bed of pelleted catalyst through which the hydrogen, ammonia and poly(oxytetramethylene) glycol are passed. When the reaction is conducted on a continuous basis, the poly(oxytetramethylene) glycol is suitably charged to the catalyst bed at the rate of about 0.1 to about 20 grams per hour of said poly(oxytetramethylene) glycol per cc of said catalyst and, more preferably, about 0.2 to about 0.6 grams per hour of poly(oxytetramethylene) glycol per cc of catalyst.

The reaction mixture formed as a result of the reductive amination of the poly(oxytetramethylene) glycol may be recovered and fractionated in any suitable manner, such as by fractional distillation, to obtain unreacted feed components, by-products and the desired poly(oxytetramethylene) diamine reaction product. Conversions of 90 wt. % or more and selectivities of 90% or more are obtainable with the process of the present invention, such that only minor quantities of unreacted feedstock and by-products are present in the reaction mixture.

EXAMPLES

The present invention will be further illustrated by the following specific examples which are given by way of illustration and which are not intended as limitations on the scope of this invention.

The nickel, copper, chromium, molybdenum catalyst used in conducting the batch and continuous experiments reported in the examples was a catalyst composed of about 75 wt. % of nickel, about 21 wt. % of copper, about 2 wt. % of chromium and about 2 wt. % of molybdenum.

In Example 1, which was conducted in an autoclave, the catalyst was powdered. In the subsequent examples, which were conducted on a continuous basis in a continuous reactor, a bed of pelleted catalyst was employed.

Example 1

A one-liter autoclave was charged with 299 g of a 2000 molecular weight poly(oxytetramethylene) glycol, 48 g of catalyst, and 90 g of ammonia. The clave was then pressured to 350 psig with hydrogen and heated over a 46-minute period to 220° C. It was held at that temperature for 3 hours. The reaction was then cooled and vented. The catalyst was removed by filtration and the product stripped at reduced pressure. The product had the following analysis:

| Total Acet. | 0.847 meq/g |
| Total Amine | 0.688 meq/g |
| Primary Amine | 0.556 meq/g |

Example 2

A. In the following examples a tubular reactor filled with a Ni—Cu—Cr—Mo catalyst was used. Hydrogen, ammonia and the polyol (a 1000 molecular weight poly(oxytetramethylene) glycol) in the proportions of Example 1 were fed to the bottom of the reactor. The crude produced was then stripped under vacuum and analyzed.

TABLE I

| Ex. | Temp °C. | Polyol SV | Total Acet. meq/g | Total Amine meq/g | Primary Amine meq/g | Total Amine % | Primary Amine % |
|---|---|---|---|---|---|---|---|
| 1 | 185 | 0.56 | 1.908 | 1.766 | 1.651 | 93 | 93 |
| 2 | 190 | 0.56 | 1.879 | 1.781 | 1.618 | 95 | 91 |
| 3 | 195 | 0.56 | 1.835 | 1.740 | 1.529 | 95 | 88 |
| 4 | 200 | 0.56 | 1.705 | 1.660 | 1.338 | 97 | 81 |
| 5 | 175 | 0.43 | 1.954 | 1.730 | 1.630 | 89 | 94 |
| 6 | 180 | 0.43 | 1.957 | 1.779 | 1.671 | 91 | 94 |
| 7 | 185 | 0.43 | 1.848 | 1.773 | 1.570 | 96 | 89 |
| 8 | 190 | 0.43 | 1.788 | 1.738 | 1.477 | 97 | 85 |
| 9 | 150 | 0.20 | 1.975 | 0.989 | 0.956 | 50 | 97 |
| 10 | 155 | 0.20 | 1.944 | 1.419 | 1.347 | 73 | 95 |
| 11 | 160 | 0.20 | 2.000 | 1.564 | 1.523 | 78 | 97 |
| 12 | 165 | 0.20 | 2.000 | 1.773 | 1.709 | 89 | 96 |
| 13 | 170 | 0.20 | 1.952 | 1.838 | 1.729 | 94 | 94 |
| 14 | 175 | 0.20 | 1.830 | 1.814 | 1.625 | 99 | 90 |
| 15 | 180 | 0.20 | 1.751 | 1.767 | 1.511 | 101 | 86 |

As can be seen in examples 1, 2, 6, 13 and 14, high total amine content as well as high primary amine content can be obtained by the process of the present invention. The examples also show that a variety of space velocities can be used and that for each space velocity there is an optimum temperature.

B. This is a comparison example conducted under the conditions of Example 2A, except as noted. In this example, Raney Ni was used as the catalyst and a 1000 molecular weight polyol was used.

TABLE II

| Temp. °C. | Polyol Space Velocity | Total Acet. meq/g | Total Amine meq/q | Primary Amine meq/g | Total Amine % | Primary Amine % |
|---|---|---|---|---|---|---|
| 180 | 0.28 | 1.911 | 1.577 | 1.286 | 83 | 82 |
| 175 | 0.28 | 1.900 | 1.550 | 1.260 | 82 | 81 |
| 185 | 0.28 | 1.609 | 1.549 | 1.172 | 96 | 76 |
| 190 | 0.20 | 1.536 | 1.512 | 1.104 | 98 | 73 |

None of the reaction conditions gave high total amine content and high primary amine content.

C. In this example conducted under the conditions of Example 1A, except as noted, a 650 molecular weight polyol and the catalyst in example A were used.

TABLE III

| Temp. °C. | Polyol Space Velocity | Total Acet. meq/g | Total Amine meq/g | Primary Amine meq/g | Total Amine % | Primary Amine % |
|---|---|---|---|---|---|---|
| 155 | 0.20 | 2.849 | 2.083 | 2.028 | 73 | 97 |
| 160 | 0.20 | 2.840 | 2.444 | 2.334 | 86 | 95 |
| 165 | 0.20 | 2.708 | 2.559 | 2.363 | 94 | 92 |
| 170 | 0.20 | 2.662 | 2.541 | 2.223 | 95 | 87 |

At 165° C. a product high in both total and primary amine was obtained.

D. In this example, conducted under the conditions of Example 1A, except as noted, a 2000 molecular weight polyol and the catalyst in example A were used:

TABLE IV

| Temp. °C. | Polyol Space Velocity | Total Acet. meq/g | Total Amine meq/g | Primary Amine meq/g | Total Amine % | Primary Amine % |
|---|---|---|---|---|---|---|
| 160 | 0.20 | 0.927 | 0.818 | 0.792 | 88 | 97 |
| 165 | 0.20 | 0.906 | 0.845 | 0.805 | 93 | 95 |
| 170 | 0.20 | 0.933 | 0.846 | 0.779 | 91 | 92 |
| 155 | 0.20 | 0.948 | 0.753 | 0.737 | 79 | 98 |

At 170° C., a product high in both total amine and primary amine was obtained.

E. This is a comparison example conducted under the conditions of Example 1A, except as noted. In this example a Ni—Cu—Cr catalyst was used and a 1000 molecular weight polyol was used.

TABLE V

| Temp. °C. | Polyol Space Velocity | Total Acet. meq/g | Total Amine meq/g | Primary Amine meq/g | Total Amine % | Primary Amine % |
|---|---|---|---|---|---|---|
| 160 | 0.20 | 1.835 | 1.314 | 1.144 | 72 | 87 |
| 165 | 0.20 | 1.773 | 1.358 | 1.147 | 77 | 84 |
| 170 | 0.20 | 1.723 | 1.411 | 1.165 | 82 | 83 |
| 175 | 0.20 | 1.686 | 1.458 | 1.178 | 86 | 80 |
| 180 | 0.20 | 1.67 | 1.461 | 1.163 | 87 | 80 |

High amination and high primary amine content were not obtained with this catalyst.

What is claimed is:

1. In a method for the catalytic reductive amination of a poly(oxytetramethylene) glycol in order to provide the corresponding poly(oxytetramethylene) diamine, in the presence of hydrogen and ammonia, the improvement for enhancing the yield of and selectivity to the poly(oxytetramethylene) diamine, which comprises the step of:
conducting said reductive amination reaction of said poly(oxytetramethylene) glycol in the presence of a catalyst consisting essentially of nickel, copper, chromium and molybdenum and containing, on an oxide-free basis, about 70 to 75 wt. % of nickel, about 20 to about 25 wt. % of copper, about 0.5 to 5 wt. % of chromium and about 1 to 5 wt. % of molybdenum,
said poly(oxytetramethylene) glycol having the formula:

$$HO-CH_2-CH_2-CH_2-CH_2-[-O-CH_2-CH_2-CH_2-CH_2-]_n-O-CH_2-CH_2-CH_2-CH_2-OH \quad (I)$$

wherein n represents 0 or a positive number having a value of 1 to about 50.

2. A method as in claim 1 wherein the catalyst is composed of about 70 to 78 wt. % of nickel, about 20 to about 25 wt. % of copper, about 0.5 to 3 wt. % of chromium and about 1 to 3 wt. % of molybdenum.

3. A method for the catalytic reductive amination of a poly(oxytetramethylene) glycol in order to provide the corresponding poly(oxytetramethylene) diamine, and for enhancing the yield of and selectivity to the poly(oxytetramethylene) diamine, which comprises contacting said poly(oxytetramethylene) glycol with excess ammonia and hydrogen in the presence of a catalyst consisting essentially of nickel, copper, chromium and molybdenum under reductive amination conditions including a temperature within the range of about 150° to about 220° C. and a pressure of about 100 to about 10,000 psig,
said catalyst consisting of, on an oxide-free basis, about 70 to 75 wt. % of nickel, about 20 to about 25 wt. % of copper, about 0.5 to 5 wt. % of chromium and about 1 to 5 wt. % of molybdenum,
said poly(oxytetramethylene) glycol having the formula:

$$HO-CH_2-CH_2-CH_2-CH_2-[-O-CH_2-CH_2-CH_2-CH_2-]_n-O-CH_2-CH_2-CH_2-CH_2-OH \quad (I)$$

wherein n represents 0 or a positive number having a value of 1 to about 50.

4. A method as in claim 3 wherein the catalyst is a pelleted catalyst consisting essentially of about 70 to 78 wt. % of nickel, about 20 to about 25 wt. % of copper, about 0.5 to 3 wt. % of chromium and about 1 to 3 wt. % of molybdenum and wherein the reaction is conducted continuously by passing the poly(oxytetramethylene) glycol, ammonia and hydrogen through a bed of said pelleted catalyst under said conditions of temperature and pressure at a space velocity of about 0.1 to about 20 grams per hour of said poly(oxytetramethylene) glycol, per cc of said catalyst.

5. A method for the continuous catalytic reductive amination of a poly(oxytetramethylene) glycol in order to provide the corresponding poly(oxytetramethylene) diamine, and for enhancing the yield of and selectivity to the poly(oxytetramethylene) diamine, said method comprising the steps of:
continuously passing said poly(oxytetramethylene) glycol, ammonia and hydrogen through a bed of a pelleted hydrogenation/dehydrogenation catalyst under reductive amination conditions including a temperature within the range of about 150° to about 220° C. and a pressure of about 100 to about 10,000 psig, at a space velocity of about 0.1 to about 20 grams per hour of said poly(oxytetramethylene) glycol per cc of said catalyst, and substantially quantitatively recovering a poly(oxytetramethylene) diamine corresponding to the poly(oxytetramethylene) glycol from the products of the reductive amination reaction, said catalyst consisting essentially of, on an oxide-free basis, about 70 to 75 wt. % of nickel, about 20 to about 25 wt. % of copper, about 0.5 to 5 wt. % of chromium and about 1 to 5 wt. % of molybdenum, said poly(oxytetramethylene) glycol having the formula:

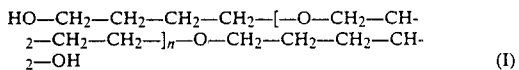
(I)

said poly(oxytetramethylene) diamine having the formula:

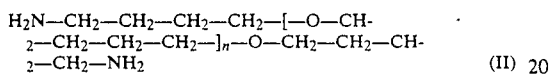
(II)

wherein n represents 0 or a positive number having a value of 1 to about 50.

6. A method as in claim 5 wherein the catalyst is a pelleted catalyst which consists essentially of, on an oxide-free basis, about 70 to 78 wt. % of nickel, about 20 to about 25 wt. % of copper, about 0.5 to 3 wt. % of chromium and about 1 to 3 wt. % of molybdenum.

7. A method for the continuous catalytic reductive amination of a selected poly(oxytetramethylene) glycol in order to provide the corresponding poly(oxytetramethylene) diamine, and for enhancing the yield of and selectivity to the poly(oxytetramethylene) diamine, said method comprising the steps of:

continuously passing said selected poly(oxytetramethylene) glycol, ammonia and hydrogen through a bed of a pelleted hydrogenation/dehydrogenation catalyst under reductive amination conditions including a reaction temperature within the range of about 165° to about 190° C., a pressure of about 100 to about 10,000 psig, at a space velocity of about about 0.2 to about 0.6 grams per hour of said poly(oxytetramethylene) glycol, per cc of said catalyst, said space velocity being correlated with the reaction temperature used for reacting the selected poly(oxytetramethylene) glycol to provide a poly(oxytetramethylene) diamine yield in excess of 90%, based on the selected poly(oxytetramethylene) glycol and selective to the primary amine in excess of 90%, based on the poly(oxytetramethylene) diamine, and recovering said poly(oxytetramethylene) diamine from the products of the reductive amination reaction, said catalyst consisting essentially of, on an oxide-free basis, about 70 to 75 wt. % of nickel, about 20 to about 25 wt. % of copper, about 0.5 to 5 wt. % of chromium and about 1 to 5 wt. % of molybdenum, said poly(oxytetramethylene) glycol having the formula:

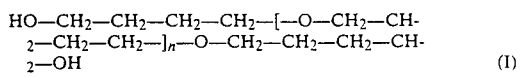
(I)

said poly(oxytetramethylene) diamine having the formula:

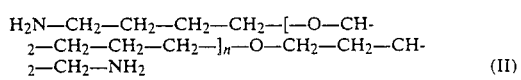
(II)

wherein n represents 0 or a positive number having a value of 1 to about 50.

* * * * *